United States Patent
Chopra

(10) Patent No.: US 10,376,178 B2
(45) Date of Patent: Aug. 13, 2019

(54) SYSTEMS AND METHODS FOR REGISTRATION OF A MEDICAL DEVICE USING RAPID POSE SEARCH

(71) Applicant: Intuitive Surgical Operations, Inc., Sunnyvale, CA (US)

(72) Inventor: Prashant Chopra, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 435 days.

(21) Appl. No.: 13/892,924

(22) Filed: May 13, 2013

(65) Prior Publication Data

US 2013/0303891 A1 Nov. 14, 2013

Related U.S. Application Data

(60) Provisional application No. 61/646,643, filed on May 14, 2012.

(51) Int. Cl.
*A61B 5/06* (2006.01)
*A61B 34/10* (2016.01)
(Continued)

(52) U.S. Cl.
CPC .............. *A61B 5/061* (2013.01); *A61B 34/10* (2016.02); *A61B 34/30* (2016.02); *A61B 5/062* (2013.01);
(Continued)

(58) Field of Classification Search
CPC ... A61B 19/50; A61B 19/5244; A61B 1/2676; A61B 2019/5251; A61B 2019/5261;
(Continued)

(56) References Cited

U.S. PATENT DOCUMENTS 6,380,732 B1 4/2002 Gilboa
6,389,187 B1 5/2002 Greenaway et al.
(Continued)

FOREIGN PATENT DOCUMENTS

WO WO-2008005953 A2 1/2008

OTHER PUBLICATIONS

International Search Report and Written Opinion for Application No. PCT/US2013/040786, dated Aug. 12, 2013, 13 pages.
(Continued)

*Primary Examiner* — Tse W Chen
*Assistant Examiner* — Jason M Ip
(74) *Attorney, Agent, or Firm* — Haynes and Boone, LLP

(57) ABSTRACT

A method comprises identifying linked anatomical structures in stored images of a patient anatomy and modeling a structure of linkage elements. Each linkage element corresponds to one of the linked anatomical structures. The method also includes modeling a portion of the patient anatomy as a plurality of search slabs and assigning each of the linkage elements to one of the plurality of search slabs. The method also includes receiving tracking data corresponding to a sensed instrument portion. The tracking data includes position information and orientation information for the sensed instrument portion. The method also includes identifying one of the plurality of search slabs which includes the position information for the sensed instrument portion and matching the sensed instrument portion to a matched linkage element from among the linkage elements assigned to the identified one of the plurality of search slabs.

22 Claims, 5 Drawing Sheets

(51) Int. Cl.
*A61B 34/20* (2016.01)
*A61B 34/30* (2016.01)
*A61B 90/00* (2016.01)
*A61B 17/00* (2006.01)

(52) U.S. Cl.
CPC ............... *A61B 5/065* (2013.01); *A61B 5/066* (2013.01); *A61B 2017/00809* (2013.01); *A61B 2034/105* (2016.02); *A61B 2034/107* (2016.02); *A61B 2034/2051* (2016.02); *A61B 2034/2061* (2016.02); *A61B 2034/301* (2016.02); *A61B 2034/303* (2016.02); *A61B 2090/365* (2016.02); *A61B 2090/3614* (2016.02); *A61B 2505/05* (2013.01); *A61B 2562/043* (2013.01)

(58) Field of Classification Search
CPC ... A61B 2019/507; A61B 5/065; A61B 5/066; A61B 8/4245; G06T 19/003
See application file for complete search history.

(56) References Cited

U.S. PATENT DOCUMENTS

| | | | |
|---|---|---|---|
| 7,599,535 B2 * | 10/2009 | Kiraly | ....................... G06T 7/60 382/128 |
| 7,901,348 B2 | 3/2011 | Soper et al. | |
| 7,930,065 B2 | 4/2011 | Larkin et al. | |
| 2006/0013523 A1 | 1/2006 | Childlers et al. | |
| 2007/0135803 A1* | 6/2007 | Belson | ............................ 606/1 |
| 2007/0167714 A1* | 7/2007 | Kiraly | .................. A61B 1/2676 600/407 |
| 2009/0156895 A1* | 6/2009 | Higgins | ................ G06T 19/003 600/104 |
| 2009/0209817 A1 | 8/2009 | Averbuch | |
| 2009/0227861 A1 | 9/2009 | Ganatra et al. | |
| 2009/0268955 A1 | 10/2009 | Koolwal et al. | |
| 2011/0184238 A1 | 7/2011 | Higgins et al. | |
| 2011/0282151 A1 | 11/2011 | Trovato et al. | |
| 2012/0069167 A1 | 3/2012 | Liu et al. | |
| 2012/0289777 A1 | 11/2012 | Chopra et al. | |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. 13790675.6, dated Apr. 4, 2016, 8 pages.

\* cited by examiner

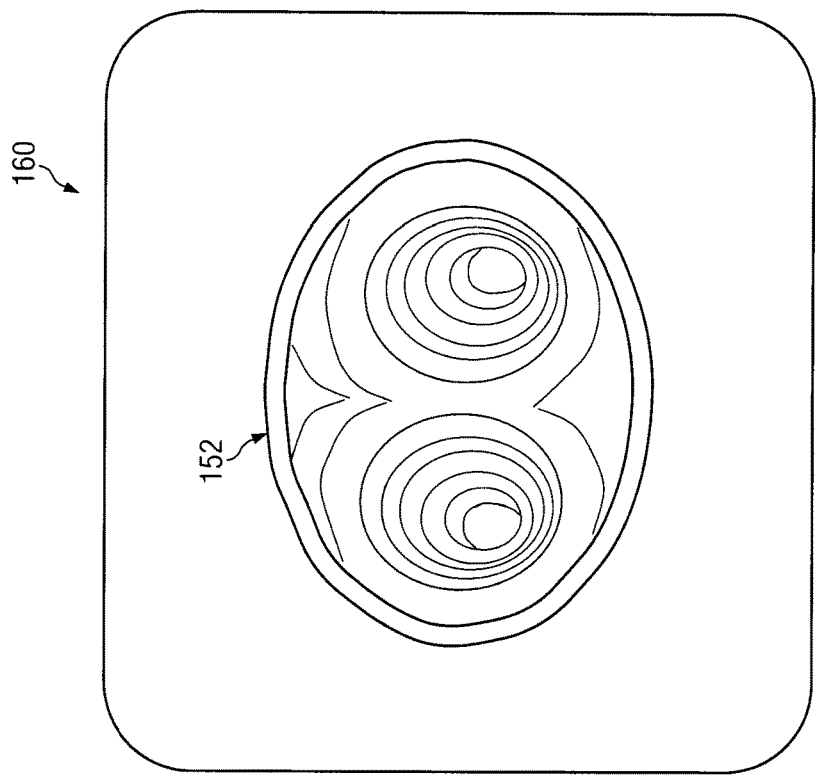
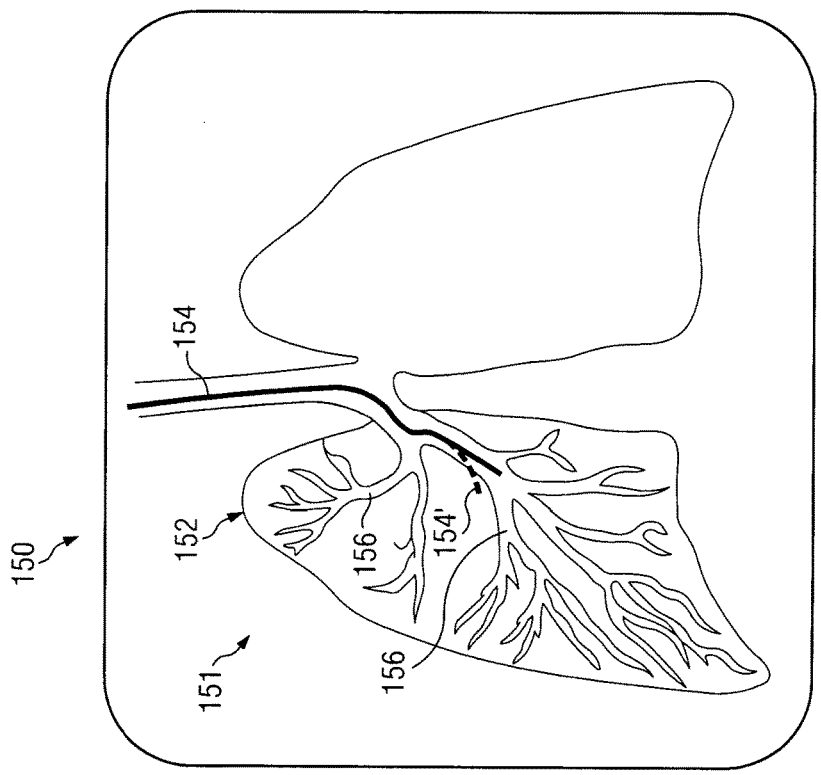
Fig. 3a
Fig. 3b

SYSTEMS AND METHODS FOR REGISTRATION OF A MEDICAL DEVICE USING RAPID POSE SEARCH

CROSS-REFERENCE TO RELATED APPLICATIONS

This application claims the benefit of U.S. Provisional Application 61/646,643 filed May 14, 2012, which is incorporate by reference herein in its entirety.

FIELD

The present disclosure is directed to systems and methods for tracking a medical device within a patient anatomy during a medical procedure, and more particularly to systems and methods for tracking a medical device within a patient anatomy using a modeled structure of the patient anatomy to conduct a rapid pose search.

BACKGROUND

Minimally invasive medical techniques are intended to reduce the amount of tissue that is damaged during diagnostic or surgical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert surgical instruments to reach a target tissue location. To reach the target tissue location, the minimally invasive surgical instruments may navigate natural or surgically created connected passageways in anatomical systems such as the lungs, the colon, the intestines, the kidneys, the heart, the circulatory system, or the like. Navigational assist systems help the clinician route the surgical instruments and avoid damage to the anatomy. These systems can incorporate the use of position and shape sensors to more accurately describe the shape, pose, and location of the surgical instrument in real space or with respect to pre-procedural or concurrent images. In a dynamic anatomical system and/or in an anatomical region dense with many anatomical passageways, accurately registering a minimally invasive instrument to the anatomical system is a time consuming and computer processing intensive task. Improved systems and methods are needed for increasing the accuracy and efficiency of systems and methods of registering minimally invasive instruments to the anatomical system.

SUMMARY

The embodiments of the disclosure are summarized by the claims that follow below.

In one embodiment, a method comprises identifying linked anatomical structures in stored images of a patient anatomy and modeling a structure of linkage elements. Each linkage element corresponds to one of the linked anatomical structures. The method also includes modeling a portion of the patient anatomy as a plurality of search slabs and assigning each of the linkage elements to one of the plurality of search slabs. The method also includes receiving tracking data corresponding to a sensed instrument portion. The tracking data includes position information and orientation information for the sensed instrument portion. The method also includes identifying one of the plurality of search slabs which includes the position information for the sensed instrument portion and matching the sensed instrument portion to a matched linkage element from among the linkage elements assigned to the identified one of the plurality of search slabs.

In another embodiment, a medical system comprises a memory storing images of a patient anatomy. The system further includes a processor for identifying linked anatomical structures in the stored images of a patient anatomy. The processor also receives the tracking data which includes position information and orientation information for a sensed instrument portion. The processor also modifies the tracking data to generate snapped position and snapped orientation information for the sensed instrument portion and renders a composite medical image. The composite medical image includes an image of at least a portion of the linked anatomical structures and an image of the sensed instrument portion in the snapped position and snapped orientation.

In another embodiment, a method comprises rendering a composite medical image that includes an image of a plurality of passageways in a patient anatomy and an image of a medical instrument. The method also includes correcting the image of the medical instrument to position a point on the medical instrument within one of the plurality of passageways in the composite medical image. The image is corrected by generating a model of the passageways, identifying one of a plurality of slabs of the model that includes a position of the medical instrument, and matching one of the passageways in the slab to the point on the medical instrument.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 3a is an image of a human lung registered with an image of a minimally invasive instrument.

FIG. 3b is an internal image of the human lung depicting the region of the human lung from the viewpoint of the minimally invasive instrument.

DETAILED DESCRIPTION

In the following detailed description of the embodiments of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
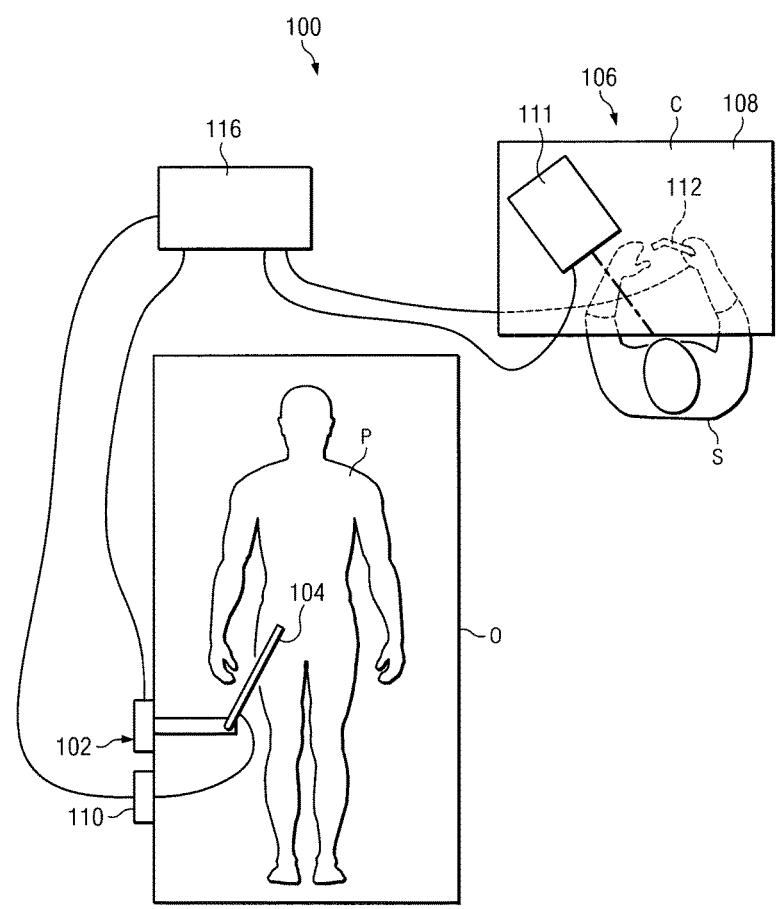
FIG. 1 is a robotic surgical system, in accordance with embodiments of the present disclosure.

Referring to FIG. 1 of the drawings, a robotic surgical system is generally indicated by the reference numeral 100. As shown in FIG. 1, the robotic system 100 generally includes a surgical manipulator assembly 102 for operating a surgical instrument 104 in performing various procedures on the patient P. The assembly 102 is mounted to or near an operating table O. A master assembly 106 allows the surgeon S to view the surgical site and to control the manipulator assembly 102.

In alternative embodiments, the robotic system may include more than one manipulator assembly. The exact number of manipulator assemblies will depend on the surgical procedure and the space constraints within the operating room among other factors.

The master assembly 106 may be located at a surgeon's console C which is usually located in the same room as operating table O. However, it should be understood that the surgeon S can be located in a different room or a completely different building from the patient P. Master assembly 106 generally includes an optional support 108 and one or more control device(s) 112 for controlling the manipulator assemblies 102. The control device(s) 112 may include any number of a variety of input devices, such as joysticks, trackballs, gloves, trigger-guns, hand-operated controllers, voice recognition devices or the like. In some embodiments, the control device(s) 112 will be provided with the same degrees of freedom as the associated surgical instruments 104 to provide the surgeon with telepresence, or the perception that the control device(s) 112 are integral with the instruments 104 so that the surgeon has a strong sense of directly controlling instruments 104. In some embodiments, the control devices 112 are manual input devices which move with six degrees of freedom, and which may also include an actuatable handle for actuating instruments (for example, for closing grasping jaws, applying an electrical potential to an electrode, delivering a medicinal treatment, or the like).

A visualization system 110 may include a viewing scope assembly (described in greater detail below) such that a concurrent or real-time image of the surgical site is provided to surgeon console C. The concurrent image may be, for example, a two or three dimensional image captured by an endoscope positioned within the surgical site. In this embodiment, the visualization system 100 includes endoscopic components that may be integrally or removably coupled to the surgical instrument 104. However in alternative embodiments, a separate endoscope, attached to a separate manipulator assembly may be used with the surgical instrument to image the surgical site. The visualization system 110 may be implemented as hardware, firmware, software or a combination thereof which interact with or are otherwise executed by one or more computer processors, which may include the processors of a control system 116 (described below).

A display system 111 may display an image of the surgical site and surgical instruments captured by the visualization system 110. The display 111 and the master control devices 112 may be oriented such that the relative positions of the imaging device in the scope assembly and the surgical instruments are similar to the relative positions of the surgeon's eyes and hands so the operator can manipulate the surgical instrument 104 and the hand control as if viewing the workspace in substantially true presence. By true presence, it is meant that the presentation of an image is a true perspective image simulating the viewpoint of an operator that is physically manipulating the surgical instruments 104.

Alternatively or additionally, monitor 111 may present images of the surgical site recorded and/or modeled preoperatively using imaging technology such as, computerized tomography (CT), magnetic resonance imaging (MRI), fluoroscopy, thermography, ultrasound, optical coherence tomography (OCT), thermal imaging, impedence imaging, laser imaging, or nanotube X-ray imaging. The presented preoperative images may include two-dimensional, three-dimensional, or four-dimensional images.

In some embodiments, the monitor 111 may display a virtual navigational image in which the actual location of the surgical instrument is registered (i.e., dynamically referenced) with preoperative or concurrent images to present the surgeon S with a virtual image of the internal surgical site at the location of the tip of the surgical instrument. An image of the tip of the surgical instrument or other graphical or alphanumeric indicators may be superimposed on the virtual image to assist the surgeon controlling the surgical instrument. Alternatively, the surgical instrument may not be visible in the virtual image.

In other embodiments, the monitor 111 may display a virtual navigational image in which the actual location of the surgical instrument is registered with preoperative or concurrent images to present the surgeon S with a virtual image of surgical instrument within the surgical site from an external viewpoint. An image of a portion of the surgical instrument or other graphical or alphanumeric indicators may be superimposed on the virtual image to assist the surgeon controlling the surgical instrument.

As shown in FIG. 1, a control system 116 includes at least one processor and typically a plurality of processors for effecting control between the surgical manipulator assembly 102, the master assembly 106, and the image and display system 110. The control system 116 also includes software programming instructions to implement some or all of the methods described herein. While control system 116 is shown as a single block in the simplified schematic of FIG. 1, the system may comprise a number of data processing circuits (e.g., on the surgical manipulator assembly 102 and/or on the master assembly 106), with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the robotic systems described herein. In one embodiment, control system 116 may support wireless communication protocols such as Bluetooth, IrDA, HomeRF, IEEE 802.11, DECT, and Wireless Telemetry.

In some embodiments, control system 116 may include servo controllers to provide force and torque feedback from the surgical instruments 104 to the hand-operated control device 112. Any suitable conventional or specialized servo controller may be used. A servo controller may be separate from, or integral with manipulator assemblies 102. In some embodiments, the servo controller and manipulator assembly are provided as part of a robotic arm cart positioned adjacent to the patient's body. The servo controller transmits signals instructing the manipulator assemblies to move instruments which extend into an internal surgical site within the patient body via openings in the body.

Each of the manipulator assemblies 102 that support a surgical instrument 104 and may comprise a series of manually articulatable linkages, generally referred to as set-up joints, and a robotic manipulator. The robotic manipulator assemblies 102 may be driven by a series of actuators (e.g., motors). These motors actively move the robotic manipulators in response to commands from the control system 116. The motors are further coupled to the surgical instrument so as to advance the surgical instrument into a naturally or surgically created anatomical orifice and to move the distal end of the surgical instrument in multiple degrees of freedom that may include three degrees of linear motion (e.g., X, Y, Z linear motion) and three degrees of rotational motion (e.g., roll, pitch, yaw). Additionally, the motors can be used to actuate an articulatable end effector of the instrument for grasping tissues in the jaws of a biopsy device or the like.

Figure 2:
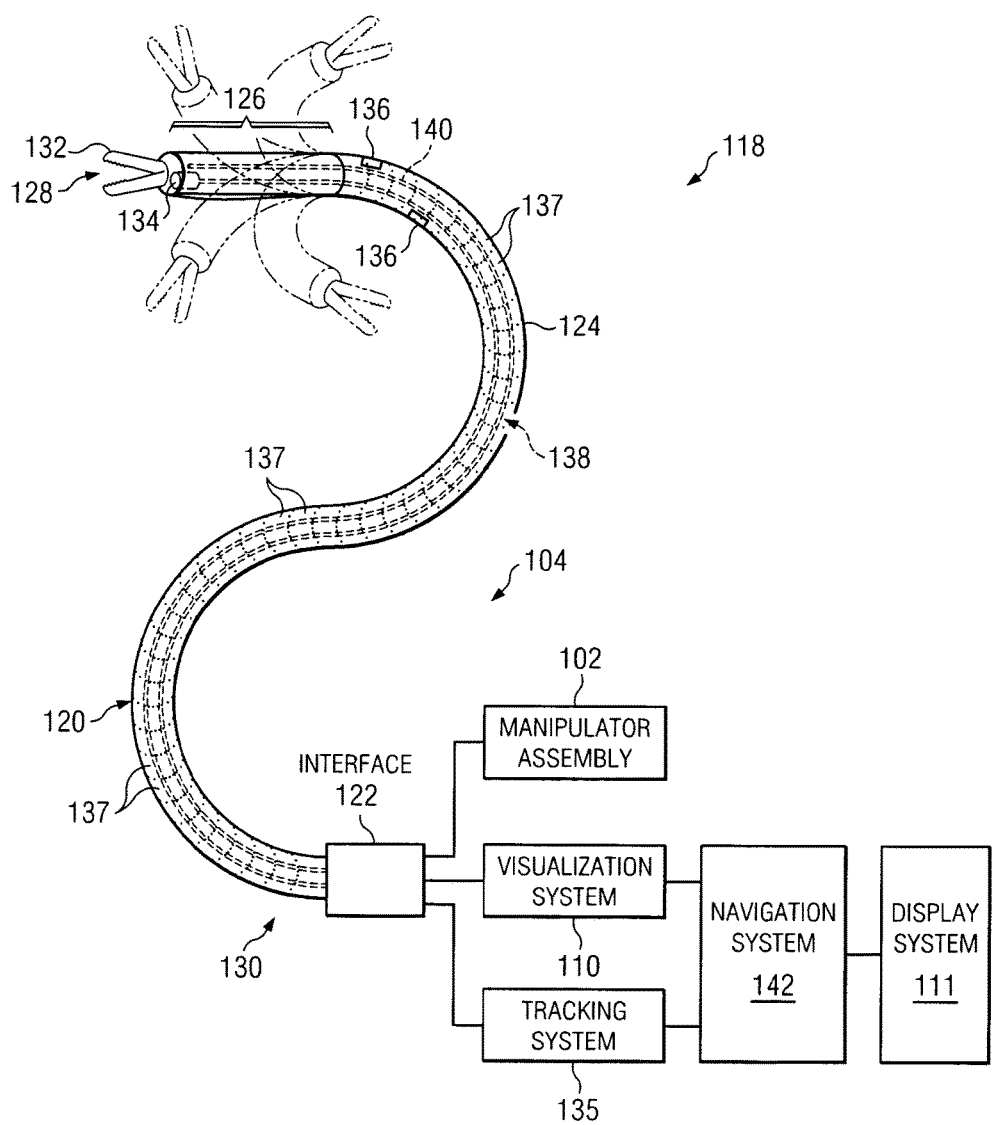
FIG. 2 illustrates a surgical instrument system utilizing aspects of the present disclosure.

FIG. 2 illustrates a tracked instrument system 118 which includes the surgical instrument system 104 and its interfacing systems. The surgical instrument system 104 includes a flexible instrument 120 coupled by an interface 122 to manipulator assembly 102 and visualization system 110. The instrument 120 has a flexible body 124, a tip 126 at its distal end 128, and the interface 122 at its proximal end 130. The body 124 houses cables, linkages, or other steering controls (not shown) that extend between the interface 122 and the tip 126 to controllably bend or turn the tip as shown for example by the dotted line versions of the bent tip 126, and in some embodiments control an optional end effector 132. The flexible instrument may be steerable, including the steering controls previously described, or may be non-steerable with no integrated mechanism for operator control of the instrument bending. The end effector may be a working distal part that is manipulable for a medical function, e.g., for effecting a predetermined treatment of a target tissue. For instance, some end effectors have a single working member such as a scalpel, a blade, or an electrode. Other end effectors such as shown in the embodiment of FIG. 2, have a pair or plurality of working members such as forceps, graspers, scissors, or clip appliers, for example. Examples of electrically activated end effectors include electrosurgical electrodes, transducers, sensors, and the like. End effectors may also include conduits to convey fluids, gases or solids to perform, for example, suction, insufflation, irrigation, treatments requiring fluid delivery, accessory introduction, biopsy extraction and the like). In other embodiments, flexible body 124 can define one or more lumens through which surgical instruments can be deployed and used at a target surgical location.

The instrument 120 can also include an image capture element 134 which may include a stereoscopic or monoscopic camera disposed at the distal end 128 for capturing images that are transmitted to and processed by the visualization system 110 for display by the display system 111. Alternatively, the image capture element 134 may be a coherent fiber-optic bundle that couples to an imaging and processing system on the proximal end of the instrument 120, such as a fiberscope. The image capture element 134 may be single or multi-spectral for capturing image data in the visible or infrared/ultraviolet spectrum.

A tracking system 135 includes an electromagnetic (EM) sensor system 136 and a shape sensor system 138 for determining the position, orientation, speed, pose, and/or shape of the distal end 128 and of one or more segments 137 along the instrument 120. Although only an exemplary set of segments 137 are depicted in FIG. 2, the entire length of the instrument 120, between the distal end 128 and the proximal end 130 and including the tip 126 may be effectively divided into segments. The tracking system 135 may be implemented as hardware, firmware, software or a combination thereof which interact with or are otherwise executed by one or more computer processors, which may include the processors of a control system 116.

The EM sensor system 136 includes one or more conductive coils that may be subjected to an externally generated electromagnetic field. Each coil of the EM sensor system 136 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point. Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

The sensor system 138 includes an optical fiber 140 aligned with the flexible body 124 (e.g., provided within an interior channel (not shown) or mounted externally). The tracking system 135 is coupled to a proximal end of the optical fiber 140. In this embodiment, the fiber 140 has a diameter of approximately 200 μm. In other embodiments, the dimensions may be larger or smaller.

The optical fiber 140 forms a fiber optic bend sensor for determining the shape of the instrument 120. In one alternative, optical fibers including Fiber Bragg Gratings (FBGs) are used to provide strain measurements in structures in one or more dimensions. Various systems and methods for monitoring the shape and relative position of a optical fiber in three dimensions are described in U.S. patent application Ser. No. 11/180,389, filed Jul. 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternative embodiments, the shape of the instrument 120 may be determined using other techniques. For example, if the history of instrument tip's pose is stored for an interval of time that is smaller than the period for refreshing the navigation display or for alternating motion (e.g., inhalation and exhalation), the pose history can be used to reconstruct the shape of the device over the interval of time. As another example, historical pose, position, or orientation data may be stored for a known point of an instrument along a cycle of alternating motion, such as breathing. This stored data may be used to develop shape information about the instrument. Alternatively, a series of positional sensors, such as EM sensors, positioned along the instrument can be used for shape sensing. Alternatively, a history of data from a positional sensor, such as an EM sensor, on the instrument during a procedure may be used to represent the shape of the instrument, particularly if an anatomical passageway is generally static. Alternatively, a wireless device with position or orientation controlled by an external magnetic field may be used for shape sensing. The history of its position may be used to determine a shape for the navigated passageways.

In this embodiment, the optical fiber 140 may include multiple cores within a single cladding 146. Each core may be single-mode with sufficient distance and cladding separating the cores such that the light in each core does not interact significantly with the light carried in other cores. In other embodiments, the number of cores may vary or each core may be contained in a separate optical fiber.

In some embodiments, an array of FBG's is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBG's, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBG's produce a reflected wavelength that is a function of the strain on the fiber and its temperature. This FBG technology is commercially available from a variety of sources, such as Smart Fibres Ltd. of Bracknell, England. Use of FBG technology in position sensors for robotic surgery is described in U.S. Pat. No. 7,930,065, filed Jul. 20, 2006, disclosing "Robotic Surgery System Including Position Sensors Using Fiber Bragg Gratings," which is incorporated by reference herein in its entirety.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. For example, regions of the cores containing FBG's, if located at points where the fiber is bent, can thereby be used to determine the amount of bending at those points. These data, combined with the known spacings of the FBG regions, can be used to reconstruct the shape of the fiber. Such a system has been described by Luna Innovations. Inc. of Blacksburg, Va.

As described, the optical fiber 140 is used to monitor the shape of at least a portion (the sensed instrument portion) of the instrument 120. More specifically, light passing through the optical fiber 140 is processed by the tracking system 135 for detecting the shape of the sensed instrument portion of the surgical instrument 120 and for utilizing that information to assist in surgical procedures. The tracking system 135 may include a detection system for generating and detecting the light used for determining the shape of the sensed instrument portion of the surgical instrument 120. This information, in turn, in can be used to determine other related variables, such as velocity and acceleration of the parts of a surgical instrument. By obtaining accurate measurements of one or more of these variables in real time, the controller can improve the accuracy of the robotic surgical system and compensate for errors introduced in driving the component parts. The sensing may be limited only to the degrees of freedom that are actuated by the robotic system, or may be applied to both passive (e.g., unactuated bending of the rigid members between joints) and active (e.g., actuated movement of the instrument) degrees of freedom.

The information from the tracking system 135 may be sent to the navigation system 142 where it is combined with information from the visualization system 110 and/or the preoperatively taken images to provide the surgeon or other operator with real-time position information on the display system 111 for use in the control of the instrument 120. The control system 116 may utilize the position information as feedback for positioning the instrument 120. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety.

In the embodiment of FIG. 2, the instrument 104 is teleoperated within the robotic surgical system 100. In an alternative embodiment, the manipulator assembly may be replaced by direct operator control. In the direct operation alternative, various handles and operator interfaces may be included for hand-held operation of the instrument.

FIG. 3a depicts a composite image 150 including an image 151 of a human lung 152, from a viewpoint external to the lung, registered with an instrument image 154 of a flexible instrument, such as the flexible instrument 120. The image 151 of the lung 152 may be generated from preoperatively recorded images or may be generated concurrently during the surgical procedure. The composite image 150 may be displayed via display system 111. As the instrument 120 is advanced through bronchial passageways 156 of the lung 152, information from the tracking system 135 and/or the visualization system 110 are used to register the instrument image 154 with the lung image 151. The image 151 of the lung 152 may change, for example, to depict the lung in a state of inspiration or expiration. The instrument image 154 may change to depict the advancement or withdrawal of the instrument 120 through the bronchial passageways 156. Occasionally, the composite image 150 may erroneously render the instrument image 154 such that a portion of the instrument image 154' is outside of a bronchial passageway. Systems and methods are described below for correcting the instrument image such that the instrument is located within the bronchial passageways.

FIG. 3b depicts an internal image 160 of the human lung 152 depicting a region of the lung from the viewpoint of the instrument 120. The image 160 may be a concurrent image taken during the surgical procedure by the instrument 120 while located in the depicted portion of the lung 152. More specifically, the image may be captured by the visualization system 110. Alternatively, the image 160 may be a preoperatively recorded image selected based upon the location of the tip of the instrument 120 as determined by the tracking system 135.

FIGS. 4a-4d depict a method of registering a point on a minimally invasive instrument, such as the flexible instrument 120, to a set of linked elements corresponding to passageways of a patient anatomy. FIG. 5. is a flowchart 300 describing the method depicted in FIGS. 4a-4d. Often, the tracking system 135, which includes the EM sensor system 136 and the shape sensor system 138 may calculate a position for the instrument tip 126 or one or more segments 137 of the instrument 120 that is outside the anatomical passageway if depicted in a composite image. This likely indicates a slight measurement error (assuming the wall of the anatomical passageway has not been breached). Such an error may result from the dynamic nature of certain anatomic structures such as the lungs or the heart. For example, inhalation and exhalation changes the position and size of the bronchial passageways of the lung. Alternatively, the error may result from tissue deformation caused by the presence of the surgical instrument within the anatomic passageways.

Figure 6:
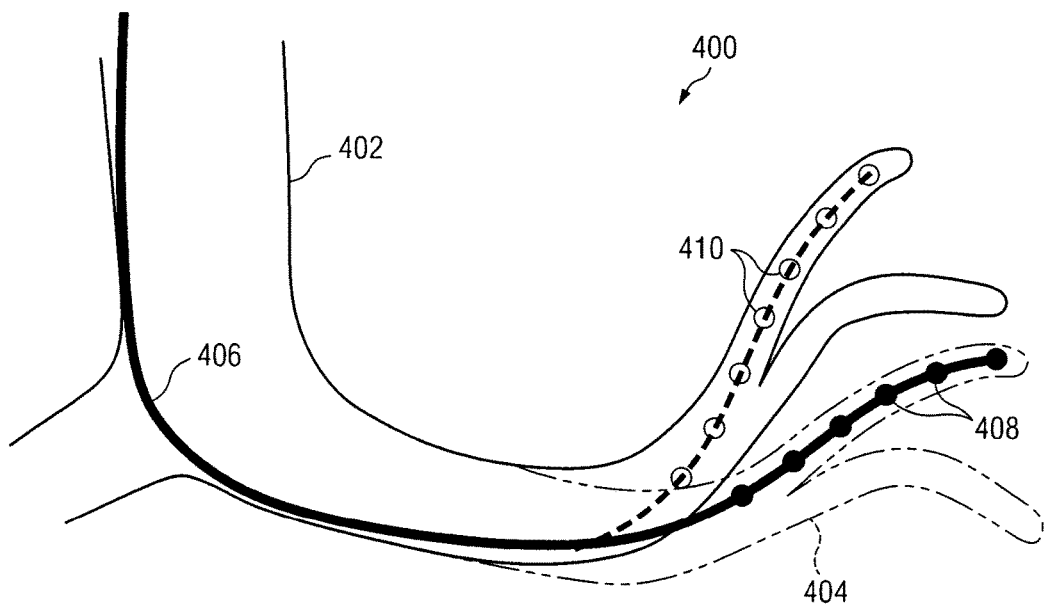
FIG. 6 illustrates an image of a portion of a set of anatomical passageways with an image of a measured device shape and a snapped device shape.

To correct the position of the instrument and accurately locate one or more points of the instrument within the passageway when the image of the instrument and the image of the patient anatomy are co-registered and displayed, selected points of the instrument may be graphically registered to a location on the wall of the anatomical passageway or to the lumen of the anatomical passageway (i.e., snapped). FIG. 6 illustrates a general snapping operation. A set of anatomical passageways 400 (e.g., bronchial passageways) is illustrated. The solid line 402 is an image of a static passageway generated by a preoperative image (or generated by another preoperative or standard anatomical dataset). The passageway as deformed by an instrument 406 is represented by dashed line 404. The actual sensed instrument shape 408 causing the deformed passageway 404 is represented by a trail of solid dots. The instrument shape 408 is the sensed instrument shape prior to any snapping adjustments. The snapped instrument shape 410 is represented by a trail of open dots. As will be described in detail below, systems and methods are provided to adjust the pose, position, or orientation of the sensed instrument shape 408 into the snapped instrument shape 410 that conforms with the shape of the preoperative image.

Methods for determining the proper location to which a point of an instrument should be snapped are described in detail below but generally include identifying linked anatomical structures in stored images of a patient anatomy and then modeling a structure of linkage elements with each linkage element corresponding to one of the linked anatomical structures. With the flexible instrument inserted into the linked anatomical structures, tracking data is received from the instrument. The tracking data includes position information and orientation information for one or more portions of the instrument. The tracking data is modified to generate snapped position and snapped orientation information for the sensed instrument portions. A composite medical image is then rendered to include an image of some portion of the linked anatomical structures and an image of the sensed instrument portion in the snapped position and snapped orientation.

Figure 4A:
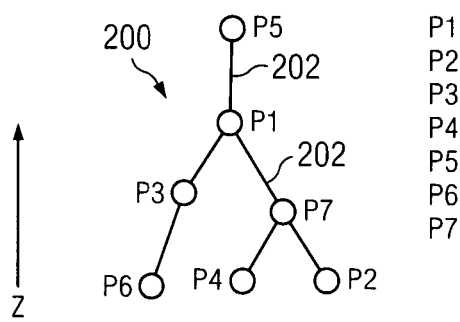
FIGS. 4a-4d depict a method of registering a portion of a minimally invasive instrument to a set of linked elements corresponding to passageways of a patient anatomy.
Figure 5:
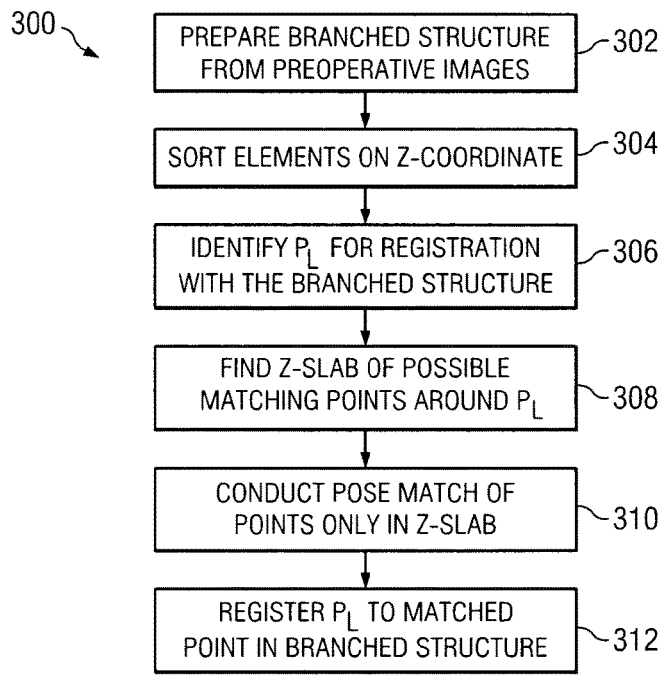
FIG. 5 is a flowchart depicting the method according to an embodiment of this disclosure.

In FIG. 4a and at step 302, a branched structure 200 of linked elements P1-P7 is modeled from preoperative images of a patient anatomy. The images may be, for example, CT images of the lung 152. The linked elements P1-P7 may correspond generally to branch points in the airway passages of the lung 152. The branched structure 200 also includes linkages 202, extending between the linked elements P1-P7, which generally correspond the bronchial passageways between the branch points in the lung 152. Initially, there may be no order associated with the linked elements P1-P7 other than the order provided by the branched structure 200. The branched structure 200 may be retained in a computer memory and optionally may be depicted on a display.

Figure 4B:
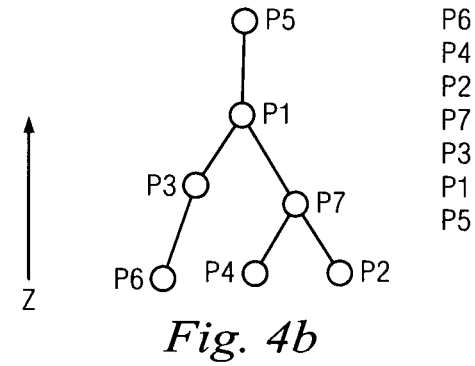

In FIG. 4b, and at step 304, the linked elements P1-P7 are sorted according to their location along a chosen axis which can be one of the three orthogonal axes spanning the patient image volument (X, Y, or Z). For example, the chosen axis may be a Z coordinate axis, e.g., an axis that corresponds generally to a caudal-cranio axis of the patient anatomy. Alternatively, the axis may be an oblique axis aligned with anatomical features such as a medial line of a large organ. In another alternative embodiment, the axis may be an axis aligned with the general direction of the planned surgical path through the anatomy.

A registry of the sorted linked elements P1-P7 may be generated and stored. For example, the order of linked elements P1-P7 according to their location along the Z axis is P6, P4, P2, P7, P3, P1, and P5. Based upon this ordering, the linked elements P1-P7 are assigned to search slabs, i.e., regions of points within predetermined distances along the Z axis. In one embodiment, a slab may have a width along the Z axis that is size constrained by the resolution of the imaging modality used to reconstruct the passageway models. For example, a slab width along the Z-axis may be approximately 0.5-0.675 mm and 0.5 mm within a layer of the imaging modality (X-axis and Y-axis). In other embodiments, the width of the slab along the Z-axis may be the entire model span. A slab may be defined to include multiple component slabs. For example, a selected 20 mm slab may include four adjoining 5 mm slabs. In another embodiment, the slabs may be a part of a hierarchical representation of the 3D space spanning the patient's anatomy (e.g., an octree). In yet another embodiment, the size of the slabs may be dynamic, being relatively large in areas of low interest to the anatomy (e.g., the trachea when the anatomy is the lungs), and progressively decreasing in size around regions of fine anatomical details (e.g., in the sub-segmental passages when the anatomy is lung).

Figure 4C:
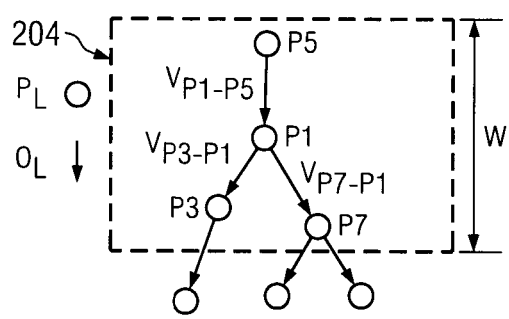

In FIG. 4c and at step 306, a point $P_L$, which may generally correspond to the tip 126 or another known point or segment 137 of the instrument 120 begins a reference procedure with the sorted linked elements P1-P7. The point $P_L$ is associated with reference information including position information and orientation information. The position information may include X, Y, Z coordinate information for the point $P_L$. The orientation information $O_L$ may include orientation information related to pitch, yaw, and roll of the instrument 120 extending from point $P_L$. At step 308, the position information for point $P_L$ is analyzed to determine a slab of points from among the points P1-P7 which have positions near the point $P_L$. For example, as shown in FIG. 4c, a slab 204, with a slab width W along the Z axis, includes the ordered points P7, P3, P1, and P5. A slab selected with a larger width may include more ordered points, and a slab selected with a smaller width may include fewer ordered points.

At step 310, within the selected slab 204 only, a pose match is conducted. A pose match includes a comparison of both the position information of point $P_L$ and orientation information $O_L$ to the pose information for each of the linked elements P7, P3, P1, and P5 and their connected linkages 202. A determination of a best match is based upon the distance of point $P_L$ to linked elements P7, P3, P1, and P5 and the alignment of orientation vector $O_L$ to the vectors $V_{P1\text{-}P5}$, $V_{P3\text{-}P1}$, or $V_{P7\text{-}P1}$. The orientation comparison requires more time and computer processing resources than the position comparison alone. Thus, by limiting the detailed orientation comparison of $P_L$ to only the points in the surrounding slab, time and processing resources may be conserved.

Figure 4D:
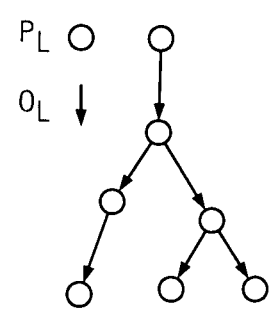

In FIG. 4d and at step 312, $P_L$ is matched based on pose to P5. Thus, the portion of the instrument 120 associated with $P_L$ is referenced to the point P5. A composite image can then be rendered depicting the point $P_L$ of the instrument 120 at the location and orientation associated with the branch point P5 of the bronchial passageway. The point $P_L$ can be snapped to the branch point P5 so that the composite image of the lung and the instrument depicts the instrument within the bronchial passageway at the point P5.

Steps 306-312 can be repeated for additional points associated with one or more surgical instruments until an accurate rendering of surgical instruments registered with surgical images is complete.

Alternative systems and methods for registering an image of at least a portion of a flexible instrument to an image of an anatomical system are disclosed in U.S. patent application Ser. No. 13/893,008, disclosing "Systems and Methods for Deformation Compensation Using Shape Sensing" and in U.S. patent application Ser. No. 13/893,040, disclosing "Systems and Methods for Registration of a Medical Device Using a Reduced Search Space," both of which are incorporated by reference herein in their entirety. Aspects of theses incorporated by reference systems and methods may be used together with the above disclosed systems and methods to provide alternative methods of accurately registering an image of at least a portion of a flexible instrument to an image of an anatomical system.

Although the registration systems and methods have been described herein with respect to teleoperated or hand operated surgical systems, these registration systems and methods will find application in a variety of medical and non-medical instruments in which accurate instrument image registration is otherwise too time consuming or computer processing intensive.

Although the systems and methods of this disclosure have been illustrated for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like. Treatments that may be performed with the systems and methods of this disclosure include exploration, biopsy, drug delivery, stenting procedures, anerysm repair, and stimulation electrode placement. The methods and embodiments of this disclosure are also suitable for non-surgical applications.

One or more elements in embodiments of the invention may be implemented in software to execute on a processor of a computer system such as control system 116. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method comprising:
   identifying linked anatomical structures in stored images of a patient anatomy;
   modeling the linked anatomical structures as a three-dimensional structure of linkage elements, wherein each linkage element corresponds to one of the linked anatomical structures;
   defining, within the three-dimensional structure of linkage elements, a portion of the three-dimensional structure of linkage elements as a plurality of search slabs dynamic in size, progressing between a first search slab having a first width along an axis of the three-dimensional structure of linkage elements in an area of low anatomical detail and a second search slab having a second width along the axis of the three-dimensional structure of linkage elements in an area of fine anatomical detail, wherein the first width is larger than the second width;
   assigning each of the linkage elements of the three-dimensional structure of linkage elements to one of the plurality of search slabs;
   receiving tracking data corresponding to a sensed instrument portion, wherein the tracking data includes position information and orientation information for the sensed instrument portion;
   identifying one of the plurality of search slabs which corresponds to a location indicated by the position information for the sensed instrument portion; and
   matching, within the identified search slab, the sensed instrument portion to a matched linkage element from among the linkage elements assigned to the identified search slab, wherein the identifying of the one of the plurality of search slabs confines the matching to the linkage elements assigned to the identified search slab.

2. The method of claim 1 further comprising:
   receiving preoperative medical images into a computer memory device to create the stored images of the patient anatomy.

3. The method of claim 1 wherein assigning each of the linkage elements to one of the plurality of search slabs includes identifying a width dimension of each of the plurality of search slabs, and wherein each width dimension is greater than a resolution of the stored images.

4. The method of claim 1 wherein matching the sensed instrument portion to the matched linkage element from among the linkage elements includes matching the orientation information and the position information of the sensed instrument portion with orientation and position information for the matched linkage element.

5. The method of claim 1 further comprising:
generating corrected position information for the sensed instrument portion to match a location of the matched linkage element.

6. The method of claim 5 further comprising:
generating a composite image of the sensed instrument portion and the patient anatomy, including generating an image of the sensed instrument portion based upon the corrected position information.

7. The method of claim 1 further comprising generating a registry including the linkage elements sorted according to relative position along the axis.

8. The method of claim 1 wherein the axis corresponds to a caudal-cranio axis.

9. The method of claim 1 wherein the axis is along a planned access path through the patient anatomy.

10. A medical system comprising:
a memory storing images of a patient anatomy; and
a processor configured for
identifying linked anatomical structures in the stored images of the patient anatomy;
generating a model of the linked anatomical structures as a structure containing linkage elements;
dividing the model into a plurality of search slabs arranged along an axis, wherein each search slab is arranged along the axis of the model and contains a subset of the linkage elements and wherein the plurality of search slabs are dynamic in size, progressing between a first search slab having a first width along the axis of the model in an area of low anatomical detail and a second search slab having a second width along the axis of the model in an area of fine anatomical detail, wherein the first width is larger than the second width;
receiving tracking data from a sensed instrument, wherein the tracking data includes position information and orientation information for a sensed instrument portion;
determining an identified search slab from the plurality of search slabs corresponding to the sensed instrument portion based on the position information;
comparing the position information and the orientation information to each linkage element of the subset of the linkage elements contained in the identified search slab to determine a matched linkage element of the subset of the linkage elements that is associated with the sensed instrument portion, wherein the determining of the identified search slab narrows the comparing to the subset of the linkage elements contained in the identified search slab;
modifying the position information and orientation information to snap the position information and orientation information for the sensed instrument portion from a sensed location to a matched location in the identified search slab of the model to generate snapped position and snapped orientation information for the sensed instrument portion; and
rendering a composite medical image, wherein the composite medical image includes an image of at least a portion of the linked anatomical structures and an image of the sensed instrument portion in the snapped position and snapped orientation.

11. The medical system of claim 10 wherein the stored images of the patient anatomy include preoperatively recorded medical images.

12. The medical system of claim 10 wherein the linked anatomical structures include an anatomical system from a group consisting of: airways of a lung, a cardiovascular system, and a brain circulatory system.

13. The medical system of claim 10 further comprising an instrument including the sensed instrument portion and a sensor adapted to provide tracking data for the sensed instrument portion.

14. The medical system claim 10 wherein dividing the model into the plurality of search slabs includes identifying a width dimension of each of the plurality of search slabs.

15. The medical system of claim 10 wherein determining the matched linkage element associated with the sensed instrument portion includes matching the orientation information and the position information of the sensed instrument portion with orientation and position information for the matched linkage element.

16. The medical system of claim 10 wherein modifying the position information and orientation information of the tracking data to generate the snapped position and snapped orientation information for the sensed instrument portion includes generating the snapped position information to match a location of the matched linkage element.

17. The medical system of claim 10 wherein the memory further comprises a registry including each linkage element sorted according to relative position along the axis.

18. The medical system of claim 17 wherein the axis corresponds to a caudal-cranio axis.

19. A method comprising:
rendering a composite medical image, wherein the composite medical image includes an image of a plurality of passageways in a patient anatomy and an image of a medical instrument; and
correcting the image of the medical instrument to position a point on the medical instrument within one of the plurality of passageways in the composite medical image, wherein correcting the image includes:
generating a model of the plurality of passageways that includes linkage elements,
defining a plurality of subsets of the linkage elements along an axis of the model wherein the plurality of subsets of the linkage elements are determined by a plurality of search slabs arranged along the axis, the plurality of search slabs dynamic in size, progressing between a first search slab having a first width along the axis in an area of low anatomical detail and a second search slab having a second width along the axis in an area of fine anatomical detail, wherein the first width is larger than the second width;
based on position information of the medical instrument, identifying a first subset of the linkage elements of the model corresponding to a location that includes a position of the point on the medical instrument, and
matching, within the first subset, a first linkage element to the point on the medical instrument to match a pose of a first candidate match point in one of the plurality of passageways to a pose of the point on the medical instrument, wherein the identifying of the first subset of the linkage elements based on the position information of the medical instrument focuses the matching on the first subset of the linkage elements.

20. The method of claim 19 further comprising displaying the corrected image of the medical instrument with the point on the medical instrument snapped to the matched one of the plurality of passageways.

21. The method of claim 19 wherein the step of correcting the image further includes assigning each of the plurality of passageways to one of the plurality of subsets of the model, wherein each of the plurality of subsets is defined by a width along the axis of the model.

22. The method of claim 19 wherein the step of matching the pose of the first candidate match point in one of the plurality of passageways in the first subset to the point on the medical instrument includes matching orientation information for the point on the medical instrument to one of the plurality of passageways in the first subset.

* * * * *